United States Patent [19]
Cova et al.

[11] Patent Number: 5,235,093
[45] Date of Patent: Aug. 10, 1993

[54] PROCESS FOR PREPARING CARBOXYLIC AMIDE ESTER

[75] Inventors: Dario R. Cova; Don B. Edwards, both of St. Louis, Mo.

[73] Assignee: Monsanto Company, St. Louis, Mo.

[21] Appl. No.: 825,891

[22] Filed: Jan. 27, 1992

[51] Int. Cl.$^5$ .................. C07K 233/56; C07K 231/02
[52] U.S. Cl. .................................... 560/155; 560/171
[58] Field of Search ....................... 560/170, 171, 155

[56] References Cited

U.S. PATENT DOCUMENTS

| | | | |
|---|---|---|---|
| 3,296,303 | 1/1967 | Nemec et al. | 260/558 |
| 3,324,179 | 6/1967 | Scholz et al. | 260/561 |
| 3,417,114 | 12/1988 | Kuceski | 260/404 |
| 4,634,551 | 1/1987 | Burns et al. | 252/102 |
| 4,659,866 | 4/1987 | Batt et al. | 564/137 |
| 4,981,987 | 1/1991 | Sugimori et al. | 556/419 |

FOREIGN PATENT DOCUMENTS

| | | |
|---|---|---|
| 0445096 | 9/1991 | European Pat. Off. . |
| 631367 | 11/1949 | United Kingdom . |
| 1108395 | 4/1986 | United Kingdom . |

*Primary Examiner*—José G. Dees
*Assistant Examiner*—Samuel Barts
*Attorney, Agent, or Firm*—R. C. Loyer

[57] ABSTRACT

A process for preparing precursors for amido containing organic peracids is disclosed wherein a diester of a dibasic acid is reacted with an amine to provide a mono amido carboxylic acid ester. The reaction is conducted in a reaction column to provide a highly selective reaction which limits the amount of diamide produced. The selective reaction is conducted with a moderate excess of diester and may be conveniently operated on a continuous basis.

13 Claims, No Drawings

PROCESS FOR PREPARING CARBOXYLIC AMIDE ESTER

This invention relates to a process for preparing amide esters of dibasic acids. More particularly this invention is directed to a process for reacting a dibasic acid with an alkyl amine in a distillation column to selectively provide the mono amido ester and avoid making large amounts of the diamide. These compounds are useful as precursors in the manufacture of detergent bleach ingredients.

BACKGROUND OF THE INVENTION

The discovery of highly stable organic peracid molecules is critical to the commercialization of detergent formulations containing peracid bleaches. Such peracids have recently been discovered which are highly crystalline and have relatively high melting points. Also, it is highly important for highly stable bleaches to be prepared in a manner which eliminates, or at least minimizes contamination from metals. Metals or metal ions are particularly deleterious to peracids because they catalyze the decomposition of the peroxygen group.

Consequently, the detergent industry requires peracids which are highly stable, have high melting points and are conveniently manufactured in high volume. Because of their high melting points both the peracids and their precursors are typically purified by precipitation or crystallization techniques. Metal ions typically present in the crystallization media become trapped in the peracid crystals and become impurities which reduce the stability of the peracid. The amount of metal ion contamination is directly related to stability of the peracid.

A recent patent, U.S. Pat. No. 4,634,551 to Burns et al describes novel, relatively stable and high melting crystalline amide peracids. Generally, the precursors to these amide peracids, that is, the amido acids, were reported to have been prepared by the reaction of the appropriate acid chloride with the appropriate amine followed by precipitation of the resulting amido acid. Stability of the ultimate amide peracids generated via this method are affected not only by metal contamination but also by the chloride impurity. Attempts to purify the peracid has proven inadequate to economically remove metals and chlorides. Even purification of the amine precurser is not adequate to provide an economical product of sufficient purity for use in preparing the peracid.

The peroxyacids found in U.S. Pat. No. 4,634,551 are represented by the the formula

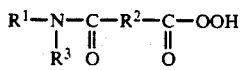

where in $R^1$ is selected from the groups consisting of alkyl, aryl or alkaryl radicals containing from about 1 to about 14 carbon atoms, $R^2$ is an alkylene group containing from 2 to 14 carbon atoms and $R^3$ is H or an alkyl, aryl or alkaryl group containing from 1 to about 10 carbon atoms, the total number of carbon atoms being from about 10 to about 20.

There is needed a process for the manufacture of large quantities of alkyl mono amido esters with a high degree of selectivity so as to minimize the simultaneous production of diamido compounds. In one effort to minimize the amount of diamido ester, a large excess of the diester is employed. This requires the movement and handling of large amounts of material because the mole ratio of diester to amine needed for improved selectivity to produce the desired mono amido ester is from 5:1 to 10:1.

The reaction of an alkyl amine with, for example, the diester of adipic acid is well known as in U.S. Pat. No. 3,417,114 to Kueski. It is noted therein that esters of mono-, di, tri, or tetracarboxlyic acids may be employed wherein the resulting amide may contain one or more ester groups, depending on the extent to which the ester groups are converted to amide groups. However, no indication is given as to how to provide a selective reaction to produce a mono amido ester of a dibasic acid.

The production of amides by reaction in a column is described in U.S. Pat. No. 3,324,179 to Scholz et al. This patent discloses the reaction of four carbon fatty acids with alkylamines wherein the amine reactant is in excess or at least in stoichiometric amounts. Reflux ratios in the range of 2:1 to 30:1 are disclosed.

The production of methyl formamide by the reaction of ammonia and methyl formate in a reaction column is disclosed in U.S. Pat. No. 4,659,866 to Kaspar et al. It is reported that virtually quantitative conversion to the amide is provided in a continuous process.

Diamides are prepared in high purity according to U.S. Pat. No. 3,296,303 to Nemec et al by the reaction of a secondary amine with a diacid or diester wherein the diester is derived from selected ethylene or propylene glycols. The amidation step is conducted by employing the amine in a ratio with the ester or acid of at least 2:1. The process seeks to avoid the production of a mixture containing mono ester amides.

Amides are also produced in the presence of water at relatively low temperatures by employing catalysts according to U.K.1,108,395. There is reference to conducting such reactions in a column. Amides are prepared at temperature of less than 30° C. with ion exchange resins, either strongly basic or strongly acid.

Although considerable work has been done in the art of preparing amides, the provision of a selective reaction of an amine with a dibasic acid to provide a high proportion of mono amido esters of such dibasic acids has not heretofore been discovered. In the production of large quantities of such material it is vital to reduce the amount of unwanted production of diamides to provide an environmentally sound mass production process.

Attempts to provide the mono amido ester of dicarboxylic acids has resulted in a relatively low yield of the desired product. The above mentioned patent to Kuceski indicates, recovery from a catalyzed reaction of about 40% by weight of the mono amido ester of adipic acid, based upon the weight of the original starting material. Other attempts to provide such product from dimethyl adipate improved over the result of Kuceski only by employing large excess of diester in the reaction mixture. Excess diester, on a molar basis, of up to 10:1 over the amine reactant in a typical batch type reaction was required to obtain up to 93% recovery of the mono amido methyl ester of adipic acid. However it is desirable to use more economical processes than can be achieved with such a large excess of starting material.

BRIEF DESCRIPTION OF THE INVENTION

In accordance with this invention there is provided a process for the preparation of a mono amido ester of a dibasic acid represented by the formula $$R^1-\underset{\underset{H}{|}}{N}-\underset{\underset{O}{\|}}{C}-R^2-\underset{\underset{O}{\|}}{C}OR^3$$

wherein $R^1$ is an alkyl group having from 4 to 12 carbon atoms, $R^2$ is an alkylene group containing from 2 to 6 carbon atoms and $R^3$ is an alkyl radical having from 1 to 4 carbon atoms which comprises the steps of introducing into a reaction column in which there is sufficient retention to provide for reaction of the amine and a diester represented by the formula $$R^3O\underset{\underset{O}{\|}}{C}-R^2-\underset{\underset{O}{\|}}{C}OR^3$$

wherein $R^2$ and $R^3$ have the same meaning as above, and an amine of the formula $$R^1NH_2$$

wherein $R^1$ has the same meaning as above, in a ratio of said ester to said amine of about 2:1, wherein the mono amido ester is removed from the column as it is produced and whereby in excess of about 95% of the amine converted to an amido compound is converted to an mono amido ester. It has been discovered that the selectivity of the reaction with respect to the production of mono amido ester is very high even though a molar ratio of ester to amine in the reaction mixture is relatively low.

DETAILED DESCRIPTION OF THE INVENTION

In the practice of this invention a trayed column is employed with a reboiler and the usual temperature control means. In continuous operation the column is operated to remove overhead low boilers produced in the reaction and to remove product from the reboiler portion of the column. Typical reflux condenser is employed to return a portion of the low boilers being removed overhead. The diester is introduced into the column at about five trays below the top of the column while the amine is introduced into the column about 20 trays from the top. A typical dibasic acid is adipic acid and it is most convenient to employ the dimethyl ester in the reaction with an amine to produce the mono amido methyl ester. In such an operation, the column is operated so as to maintain a temperature in the reboiler in the range of from about 200° C. to about 225° C. while the top is maintained in the range of from about 45° C. to about 55° C. Suitable adjustment of these temperatures can be made to provide for compounds of different molecular weight within the scope of this invention.

A continuous process is preferred wherein the product is continuously removed from the bottom of the column and the alcohol by-product removed continuously overhead. Small amounts of the diamide are also removed from the bottom of the column along with the mono amido ester which is easily separated in a subsequent step.

It has been found that optimum conversion to the mono amido ester is achieved at a reactant ratio of diester to amine of about 2:1. Higher ratios may be employed but the need to handle larger amounts of reactants is not accompanied by corresponding increase in conversion to the mono amido ester.

While not operating the process in an anhydrous mode, it has been found that too much water in the column drastically decreases the yield of desired product and causes hydrolysis of the amide to produce an acid. Therefore, the amount of water allowed in the system is in the range of about 0.05% to about 0.25% of the total weight of the diester in the column. Water produced in the manufacture of the diester must be reduced to a very low level prior to introduction into the process of this invention.

Typical dibasic acids include those having from 2 to 6 carbon atoms between the carboxyl groups. Preferably, the dibasic acids useful in this invention contain from about 3 to 5 carbon atoms between the carboxyl groups and are aliphatic, straight chained. Included are adipic acid, glutaric acid, succinic acid, pimelic acid and suberic acid.

Amines employed in the process of this invention are primary amines containing either straight or branched chain alkyl groups. Typically the amine contains from 4 to 12 carbon atom. Such amines are commercially available. Typical amines include octylamine, nonylamine and decylamine. The linear straight chain alkyl amines are preferred because the final amido acid has higher melting points than branched chained amido acids.

As noted above the reactants, diester and amine are introduced into a reaction column at the above noted areas of the column and allowed to react in the column while the alcohol by-product and desired mono amido ester are continuously removed. By sizing the column and adjusting the flow rates of reactants the reaction time or holding time in the column is regulated. It has been found that an adequate amount of reaction time in the column is essential to providing high conversion of the amine to the mono amino ester. The reaction time is controlled by the retention in the column particularly in the area between the feed trays. Retention time is controlled by regulating the feed rate and the reflux ratio. Reaction times in the range of from about 20 to about 60 minutes has been found to be adequate and a reaction time of about 40 minutes is preferred. Such times refer to the retention time in the area of the column between the feed trays.

From the above, it can be seen that it is important to maintain the reactants in the column while allowing the alcohol produced in the reaction to leave the column relatively quickly. For this reason the amine of the formula $R^1NH_2$ is chosen so as to have a lower boiling point than the diester and also to have a higher boiling point than the resultant alcohol produced in the reaction. These choices can be made by the choice of alkyl or alkylene groups in the respective reactants. A reasonable spread of boiling points is desirable such that ordinary distillation equipment may be employed to achieve both the desired retention of reactants for the purpose of reaction as well as efficient separation of product and by-product from the reaction mixture in the column.

To provide adequate separation of the desired product from the column, it is preferred to operate the process of this invention at a reflux ratio in the range of from about 20 to 1 to about 60 to 1 and more preferably in the range of from about 35 to 1 to about 40 to 1. Of course, the reaction producing the desired mono amido ester is provided at any reflux ratio which maintains the desired retention time in the column and the reflux ratio noted above provides the desired degree of product separation.

DESCRIPTION OF THE PREFERRED EMBODIMENTS

EXAMPLE 1

To demonstrate the process of this invention an Oldershaw column having a diameter of 2.54 centimeters and containing 30 trays was employed. A feed tray for the dimethyl adipate feed was provided between the 25th and 26th trays from the bottom and a feed tray for the nonylamine feed was provided between the 10th and 11th trays from the bottom. Pressure at the top of the column was maintained at 300 mm Hg absolute. Dimethyl adipate at ambient temperature was fed to the column at 58 gram/hr, and nonylamine at ambient temperature was fed to the column at 21.8 gram/hr. Heat input to the reboiler was maintained at a level sufficient to distill off the methanol evolved from the reaction at a reflux ratio of 36/1. Enough liquid was maintained in the column to give a retention time in the column of 44 minutes based on total feed to the column. The overflow from the reboiler contained the product nonyl amido methyl adipate, by product dinonyl adipate and excess dimethyl adipate. Analysis of this overflow allowed calculation of selectivity for nonyl amido adipate. For nonyl amine this was about 95% and for dimethyl adipate about 97% where selectivity is defined as the percentage of reactant producing nonyl amido methyl adipate versus that producing said product plus dinonyl adipate.

EXAMPLE 2

Employing the apparatus as described in Example 1, dimethyl adipate at ambient temperature was fed to the column at 81.3 gram/hr and nonyl amine at ambient temperature was fed to the column at 34.6 gram/hr. Heat input to the reboiler was maintained at a level sufficient to distill off the evolved methanol at a reflux ratio of 6/1. Enough liquid was maintained in the column to give a retention time in the column of about 5.4 minutes based on total feed to the column. In this case selectivity was considerably lower than in Example 1. Selectivity of nonyl amine was about 65% and for dimethyl adipate about 78%. This experiment shows the importance of retention time in the column to achieve maximum conversion and selectivity of the amine to produce mono amido methyl adipate.

Although the invention has been described in terms of specific embodiments which are set forth in considerable detail, it should be understood that this description is by way of illustration only and that the invention is not necessarily limited thereto since alternative embodiments and operating techniques will become apparent to those skilled in the art in view of this disclosure. Accordingly, modification are contemplated which can be made without departing from the spirit of the described invention.

What is claimed is:

1. A process for the preparation of a mono amido ester of a dibasic acid represented by the formula $$R^1-\overset{H}{\underset{|}{N}}-\overset{O}{\underset{\|}{C}}-R^2-\overset{O}{\underset{\|}{C}}OR^3$$

wherein $R^1$ is an alkyl group having from 8 to 10 carbon atoms, $R^2$ is an alkylene group containing from 2 to 6 carbon atoms and $R^3$ is an alkyl radical having from 1 to 4 carbon atoms in a trayed reaction column equipped with a reboiler which comprises the steps of introducing into a reaction column at about 5 trays from the top of said column a diester represented by the formula $$R^3O\overset{O}{\underset{\|}{C}}-R^2-\overset{O}{\underset{\|}{C}}OR^3$$

wherein $R_2$ and $R^3$ have the same meaning as above, and at about 20 trays from the top of said column an amine of the formula $$R^1NH_2$$

wherein $R^1$ has the same meaning as above, in a ratio of said diester to said amine of about 2:1, to provide a hold time for said ester and amine in a reaction zone between said feed trays of from about 20 minutes to about 60 minutes wherein the mono amido ester is removed from the column through said reboiler as it is produced and whereby at least about 95% of the amine converted to an amido compound is in the form of a mono amido ester.

2. The process of claim 1 wherein the amine is n-nonylamine.

3. The process of claim 2 wherein $R^3$ is methyl.

4. The process of claim 3 wherein $R^2$ contains 4 carbon atoms.

5. The process of claim 4 wherein the bottom temperature is in the range of from about 200° C. to about 225° C. and the top temperature is in the range of about 45° C. to about 55° C.

6. The process of claim 1 wherein the process is carried out in a continuous manner wherein the alcohol produced in the reaction is removed from the top of the column and the mono amido ester is removed from the bottom.

7. The process of claim 1 wherein the reboiler is provided at about ten trays below the amine feed inlet.

8. The process of claim 1 wherein the reflux ratio is in the range of from about 20 to 1 to about 60 to 1.

9. The process of claim 8 wherein the reflux ratio is in the range of from about 35 to 1 to about 40 to 1.

10. A continuous process for preparing nonyl amido methyl adipate which comprises feeding into a distillation column having at least about 30 plates dimethyl adipate at about the 5th tray from the top of the column and nonyl amine at about 20 trays from the top of the column in a weight ratio of ester to amine of about 2:1, said feed rate and reflux ratio being sufficient to provide a residence time in the column in the range of from about 20 to about 60 minutes in the section of said column between the feed trays, maintaining a temperature at the bottom of said column in the range of from about 200° C. to about 225° C. and a temperature at the top of the column in the range of from about 45° C. to about 55° C., while removing methanol from the top of the column and nonyl amido methyl adipate from the bottom whereby at least about 95% of the amine converted to an amido compound is in the form of nonyl amido methyl adipate.

11. The process of claim 10 wherein the reboiler is provided in said column at about 10 trays below the amine feed inlet.

12. The process of claim 11 wherein the reflux ratio is in the range of from about 20 to 1 to 60 to 1.

13. The process of claim 12 wherein the reflux ratio is in the range of from about 35 to 1 to about 40 to 1.

* * * * *